US012733812B2

(12) United States Patent
Watanabe et al.

(10) Patent No.: US 12,733,812 B2
(45) Date of Patent: Sep. 15, 2026

(54) OPTICAL PROBE AND AN OPTICAL TOMOGRAPHIC IMAGING APPARATUS INCLUDING THE SAME

(71) Applicant: GENESIS MEDTECH JAPAN CO., LTD., Tokyo (JP)

(72) Inventors: Hiroki Watanabe, Saitama (JP); Koji Matsumoto, Saitama (JP); Shotaro Sano, Saitama (JP); Hidenori Suzuki, Saitama (JP); Kenji Taira, Musashino (JP)

(73) Assignee: GENESIS MEDTECH JAPAN CO., LTD., Tokyo (JP)

( * ) Notice: Subject to any disclaimer, the term of this patent is extended or adjusted under 35 U.S.C. 154(b) by 0 days.

(21) Appl. No.: 18/119,133

(22) Filed: Mar. 8, 2023

(65) Prior Publication Data

US 2023/0218171 A1 Jul. 13, 2023

Related U.S. Application Data

(63) Continuation of application No. PCT/JP2020/034080, filed on Sep. 9, 2020.

(51) Int. Cl.
*A61B 5/00* (2006.01)

(52) U.S. Cl.
CPC .......... *A61B 5/0066* (2013.01); *A61B 5/6851* (2013.01)

(58) Field of Classification Search
CPC ............................ A61B 5/6851; A61B 5/0066
See application file for complete search history.

(56) References Cited

U.S. PATENT DOCUMENTS 8,380,037 B2 * 2/2013 Maruyama ........... A61B 5/0066 385/146
10,234,676 B1 3/2019 Elmaanaoui
(Continued)

FOREIGN PATENT DOCUMENTS

CN 204318703 U 5/2015
JP 2007-29653 A 2/2007
(Continued)

OTHER PUBLICATIONS

Extended European Search Report for European Application No. 20953227.4, dated May 6, 2024.
(Continued)

*Primary Examiner* — Patricia J Park
(74) *Attorney, Agent, or Firm* — Birch, Stewart, Kolasch & Birch, LLP

(57) ABSTRACT

An optical probe 40 used for the vascular optical tomographic imaging apparatus 100 includes an optical fiber 10 having a central axis 14 and a translucent lens member 20 fixed to a tip surface 12 of the optical fiber. The lens member has an outer circumferential surface surrounding an extension axis 22 obtained by extending the central axis 14 of the optical fiber forward, a rear end surface 26 intersecting the extension axis, and a tip surface 28 intersecting the extension axis. The tip surface of the lens member is a surface extending obliquely with respect to the extension axis. The outer circumferential surface of the lens member has, at least in part, a cylindrical surface portion 24 around the extension axis or a cylindrical surface portion about an axis parallel to the extension axis. The optical probe is configured so that light emitted from the tip of the optical fiber is incident on the tip surface along the extension axis, and light reflected by the tip surface is emitted from the lens member through the cylindrical surface portion.

12 Claims, 5 Drawing Sheets

(56) References Cited

U.S. PATENT DOCUMENTS

| | | | | |
|---|---|---|---|---|
| 2006/0067620 | A1 | 3/2006 | Shishkov et al. | |
| 2008/0021275 | A1 | 1/2008 | Tearney et al. | |
| 2009/0262361 | A1 | 10/2009 | Tanioka et al. | |
| 2010/0253949 | A1 | 10/2010 | Adler et al. | |
| 2011/0237958 | A1 | 9/2011 | Onimura | |
| 2013/0219969 | A1 * | 8/2013 | Bhagavatula | B29D 11/00692 65/378 |
| 2016/0018581 | A1 * | 1/2016 | Maruyama | A61B 1/07 362/551 |
| 2016/0143517 | A1 * | 5/2016 | Vance | A61B 1/00188 600/177 |
| 2018/0087893 | A1 * | 3/2018 | Sasaki | G01N 21/4795 |
| 2018/0177404 | A1 * | 6/2018 | Liu | A61B 5/0084 |
| 2019/0099237 | A1 | 4/2019 | Booker et al. | |
| 2019/0227297 | A1 | 7/2019 | Wu | |

FOREIGN PATENT DOCUMENTS

| | | | |
|---|---|---|---|
| JP | 4997112 | B2 | 8/2012 |
| JP | 2013-524930 | A | 6/2013 |
| JP | 5254865 | B2 | 8/2013 |
| JP | 5384944 | B2 | 1/2014 |
| JP | 2016-512616 | A | 4/2016 |
| JP | 2019-164330 | A | 9/2019 |
| JP | 2019-164331 | A | 9/2019 |
| WO | WO 2014/142789 | A1 | 9/2014 |

OTHER PUBLICATIONS

English translation of the International Search Report for International Application No. PCT/JP2020/034080, dated Nov. 2, 2020.

International Preliminary Report on Patentability for International Application No. PCT/JP2020/034080, dated Mar. 9, 2023.

* cited by examiner

29
IIB
28
22
24
20
12
26
30
400
18
z
16
x
y
14
40
10

OPTICAL PROBE AND AN OPTICAL TOMOGRAPHIC IMAGING APPARATUS INCLUDING THE SAME

CROSS REFERENCE TO RELATED APPLICATION

This application is a Continuation of PCT International Application No. PCT/JP2020/034080, filed on Sep. 9, 2020, which is hereby expressly incorporated by reference into the present application.

TECHNICAL FIELD

The present invention relates to an optical probe and an optical tomographic imaging apparatus including the same.

BACKGROUND ART

Patent Literature 1 (Japanese Patent No. 5384944) and 2 (Japanese Patent No. 4997112) disclose a vascular optical tomographic imaging apparatus. These optical tomographic imaging apparatuses include an optical probe and a rotation drive unit that rotates the optical probe about a longitudinal central axis thereof. At the time of imaging, the optical probe is inserted into, for example, a blood vessel, and a tomographic image of the blood vessel can be obtained by driving a rotation drive unit coupled to a proximal end of the optical probe to pull back the optical probe while rotating the optical probe at a high speed (about 180 rotations per 1 second).

The optical probe disclosed in Patent Literature 1 includes an optical fiber, a rod type lens fusion-spliced to a tip of the optical fiber, and a prism fused to a tip of the rod type lens on an opposite side from the optical fiber. In the optical probe of this form, the optical fiber can be appropriately bent along the blood vessel, but the rigid rod type lens and the prism provided at the tip cannot be easily bent. Therefore, it is conceivable that it is difficult to insert the optical probe from the main branch toward the target small branch at the bifurcation area of the blood vessel.

Another optical probe disclosed in Patent Literature 2 and 3 (Japanese Patent No. 5254865) includes a lateral-illumination ball lens at the tip of a lens portion attached to the tip of an optical fiber. This optical probe has a smaller number of components and also a shorter length of the lens portion provided at the tip than the optical probe of Patent Literature 1, so that the optical probe can be easily inserted from the main branch to the target small branch at the bifurcation area of the blood vessel.

However, it is not always easy to fabricate the size and shape of the ball lens formed at the tip of the glass rod into a target size and shape, and thus the yield of the glass rod is poor, resulting in a decrease in productivity of the optical probe. In addition, when an asymmetric ball lens having a large mass is rotated at a high speed, vibration is likely to occur, and thus, there is a risk that a captured image contains a large number of noises.

CITATION LIST

Summary of Invention

Thus, the present invention provides an optical probe that has a small number of components, can be easily inserted from a main branch to a small branch at a bifurcation area of a vessel such as a blood vessel, and can suppress vibration during rotation as much as possible, and an optical tomographic imaging apparatus including the optical probe.

Solution to Problem

In order to achieve this object, an optical probe used for a vascular optical tomographic imaging apparatus according to an embodiment of the present invention includes:

an optical fiber having a central axis; and a lens member having translucency fixed to a tip surface of the optical fiber, wherein the lens member has an outer circumferential surface surrounding an extension axis extending the central axis of the optical fiber, a rear end surface intersecting the extension axis, and a tip surface intersecting the extension axis, wherein a tip surface of the lens member is a surface extending obliquely with respect to the extension axis, wherein a rear end surface of the lens member is directly connected and optically coupled to a tip of the optical fiber, wherein the outer circumferential surface of the lens member has, at least in part, a cylindrical surface portion about the extension axis or a cylindrical surface portion about an axis parallel to the extension axis, and wherein light emitted from a tip of the optical fiber is configured to be incident on the tip surface along the extension axis, and light reflected by the tip surface is configured to be emitted from the lens member through the cylindrical surface portion.

ADVANTAGEOUS EFFECTS OF INVENTION

Brief Description of Drawings

The present invention will become more fully understood from the detailed description given hereinbelow and the accompanying drawings which are given by way of illustration only, and thus are not limitative of the present invention, and wherein.

DESCRIPTION OF EMBODIMENTS

Hereinafter, embodiments of an optical probe according to the present invention will be described with reference to the accompanying drawings.

[Optical Tomographic Imaging Apparatus]

Figure 1:
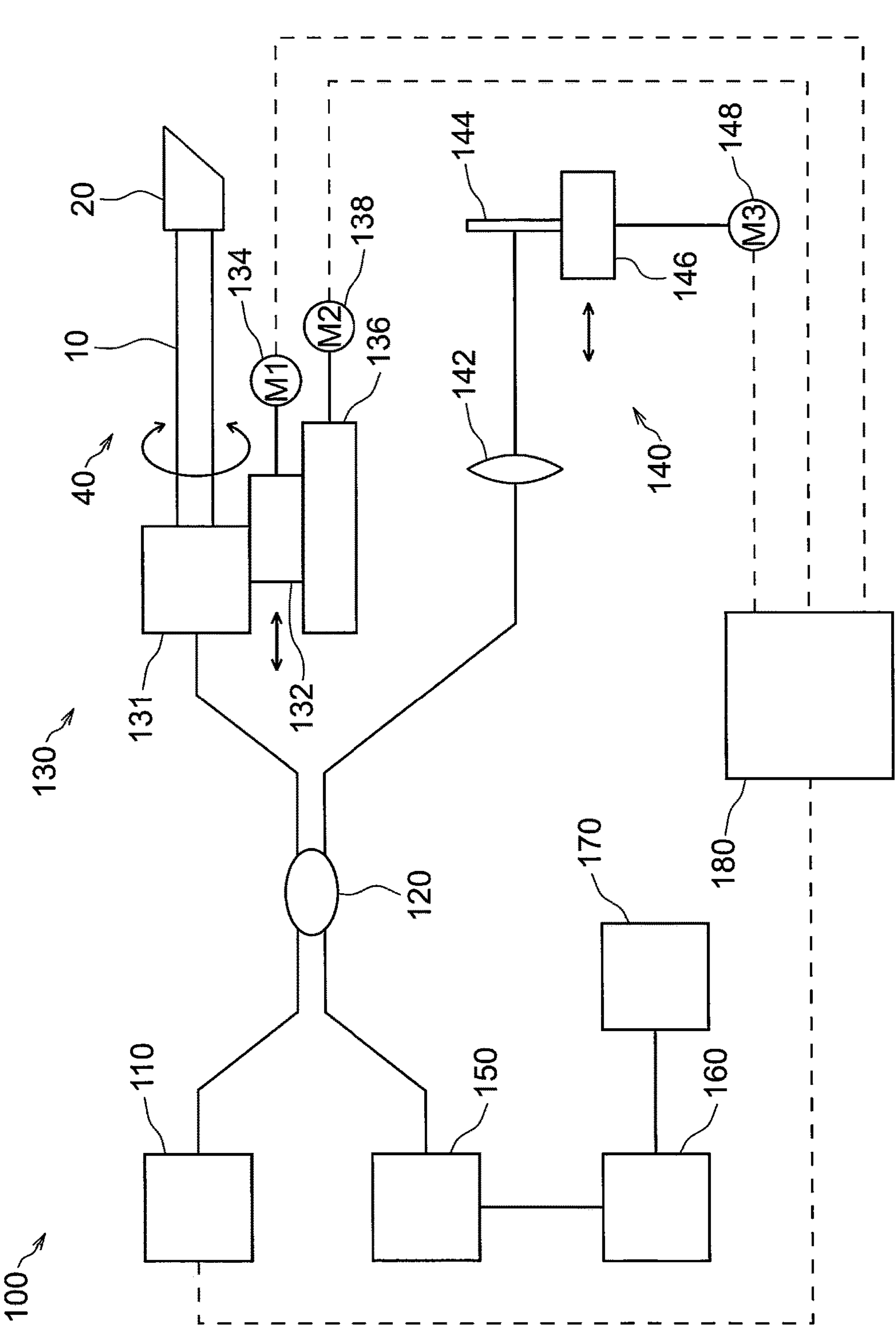
FIG. 1 is a schematic view showing a configuration of an optical tomographic imaging apparatus including an optical probe according to an embodiment of the present invention.

FIG. 1 shows an overview of an optical tomographic imaging apparatus (In general, it is referred to as optical coherence tomography or OCT.) including an optical probe according to an embodiment.

The optical tomographic imaging apparatus 100 includes: a low-coherence light source 110 that outputs light used for capturing, an optical coupler (optical splitter) 120 that branches the light sent from the low-coherence light source 110, an optical probe 40 to be described below that applies light branched from the optical coupler 120 toward a vessel such as an artery or a lymph, a motor drive unit 130 that rotates and linearly moves the optical probe 40, an optical path adjustment unit 140 that obtains reference light based on light branched from the optical coupler 120, a light receiving unit 150 that receives coherent light obtained by superimposing reflected light transmitted from the optical probe 40 and the reference light by an optical coupler 120, a signal processing unit 160 that restores an image from a signal included in the received coherent light, and a monitor 170 that displays the restored image. The low-coherence light source 110, the optical coupler 120, the optical probe 40, the motor drive unit 130, the optical path adjustment unit 140, and the light receiving unit 150 are optically connected to each other by an optical fiber so as to transmit light. In addition, the light receiving unit 150, the signal processing unit 160, and the monitor 170 are connected so as to be able to electrically communicate a signal included in the coherent light.

The low-coherence light source 110 is configured to emit light having a wavelength within a range of 700 to 1800 nm and a coherence length of about 1 μm to 100 μm (that is, generally near infrared rays).

In the embodiment, the optical coupler 120 is an optical component formed by heat-fusing two optical fibers arranged in parallel so that a fused portion is one optical fiber having a reduced diameter. The optical coupler 120 has four ports, and the respective ports are connected to the low-coherence light source 110, the motor drive unit 130, the optical path adjustment unit 140, and the light receiving unit 150. In addition, the optical coupler 120 is configured to, for example, branch light incident from the low-coherence light source 110 toward the motor drive unit 130 and the optical path adjustment unit 140, superimpose reflected light sent from the motor drive unit 130 on reference light sent from the optical path adjustment unit 140 to generate coherent light, and transmit the coherent light to the light receiving unit 150.

The motor drive unit 130 includes an optical rotary joint 131 connected to an optical fiber 10 included in an optical probe 40 described below. The optical rotary joint 131 is configured to transmit light bidirectionally between the optical coupler 120 and the optical probe 40. In addition, the optical rotary joint 131 is supported by the optical probe drive unit 132. The optical probe drive unit 132 includes an optical probe rotary motor 134, the optical probe rotary motor 134 is drivingly coupled to the optical probe drive unit 132, and based on the drive of the optical probe rotary motor 134, the optical probe drive unit 132, the optical rotary joint 131 supported by the optical probe drive unit 132, and the optical fiber 10 connected to the optical rotary joint 131 are configured to rotate about the central axis of the optical fiber 10. Furthermore, the optical probe drive unit 132 is supported by an optical probe linear drive unit 136 that moves the optical probe drive unit 132 in the central axis direction of the optical fiber 10. The optical probe linear drive unit 136 includes an optical probe linear motor 138, the optical probe linear motor 138 is drivingly coupled to the optical probe linear drive unit 136, and based on the drive of the optical probe linear motor 138, the optical probe linear drive unit 136, the optical probe drive unit 132 supported by the optical probe linear drive unit 136, the optical rotary joint 131 supported by the optical probe drive unit 132, and the optical fiber 10 connected to the optical rotary joint 131 are configured to move along the central axis direction of the optical fiber 10.

The optical path adjustment unit 140 includes a collimation lens 142 and a reference mirror 144, and is configured so that the light transmitted from the optical coupler 120 is incident on the reference mirror 144 through the collimation lens 142, and the light (reference light) reflected by the reference mirror 144 is transmitted to the optical coupler 120 through the collimation lens 142. The reference mirror 144 is supported by the mirror linear drive unit 146 that moves the reference mirror 144 in a direction toward the collimation lens 142. The mirror linear drive unit 146 includes a mirror linear motor 148, the mirror linear motor 148 is drivingly coupled to the mirror linear drive unit 146, and based on the drive of the mirror linear motor 148, the mirror linear drive unit 146 and the reference mirror 144 supported by the mirror linear drive unit 146 are configured to move toward the collimation lens 142. Therefore, the optical path adjustment unit 140 is configured to appropriately adjust the propagation distance of the reference light reflected by the reference mirror 144 and transmitted to the optical coupler 120 by driving the mirror linear drive unit 146 to move the reference mirror 144.

The light receiving unit 150 is an optical component such as a photodiode that receives and photoelectrically converts coherent light obtained by superimposing, at the optical coupler 120, the reflected light transmitted from the optical probe 40 described below and the reference light transmitted from the optical path adjustment unit 140.

In the embodiment, the signal processing unit 160 includes an amplifier (not shown) that amplifies the electric signal transmitted from the light receiving unit 150, an A/D converter (not shown) that converts the electric signal (analog signal) amplified by the amplifier into a digital signal, and an image demodulator (not shown) that reconstructs an image from the digital signal obtained by the A/D converter. Therefore, the signal processing unit 160 can reconstruct an image captured by the optical probe 40 described below and display the image on the monitor 170.

The monitor 170 is, for example, a liquid crystal display, and is configured to display an image captured by the optical probe 40 described below on the display based on an image signal transmitted from the signal processing unit 160.

The low-coherence light source 110, the optical probe rotary motor 134, the optical probe linear motor 138, and the mirror linear motor 148 are connected to the controller 180, and are configured to control outputs based on instructions transmitted from the controller 180 during capturing by the optical tomographic imaging apparatus 100.

[Optical Probe]

Figure 2A:
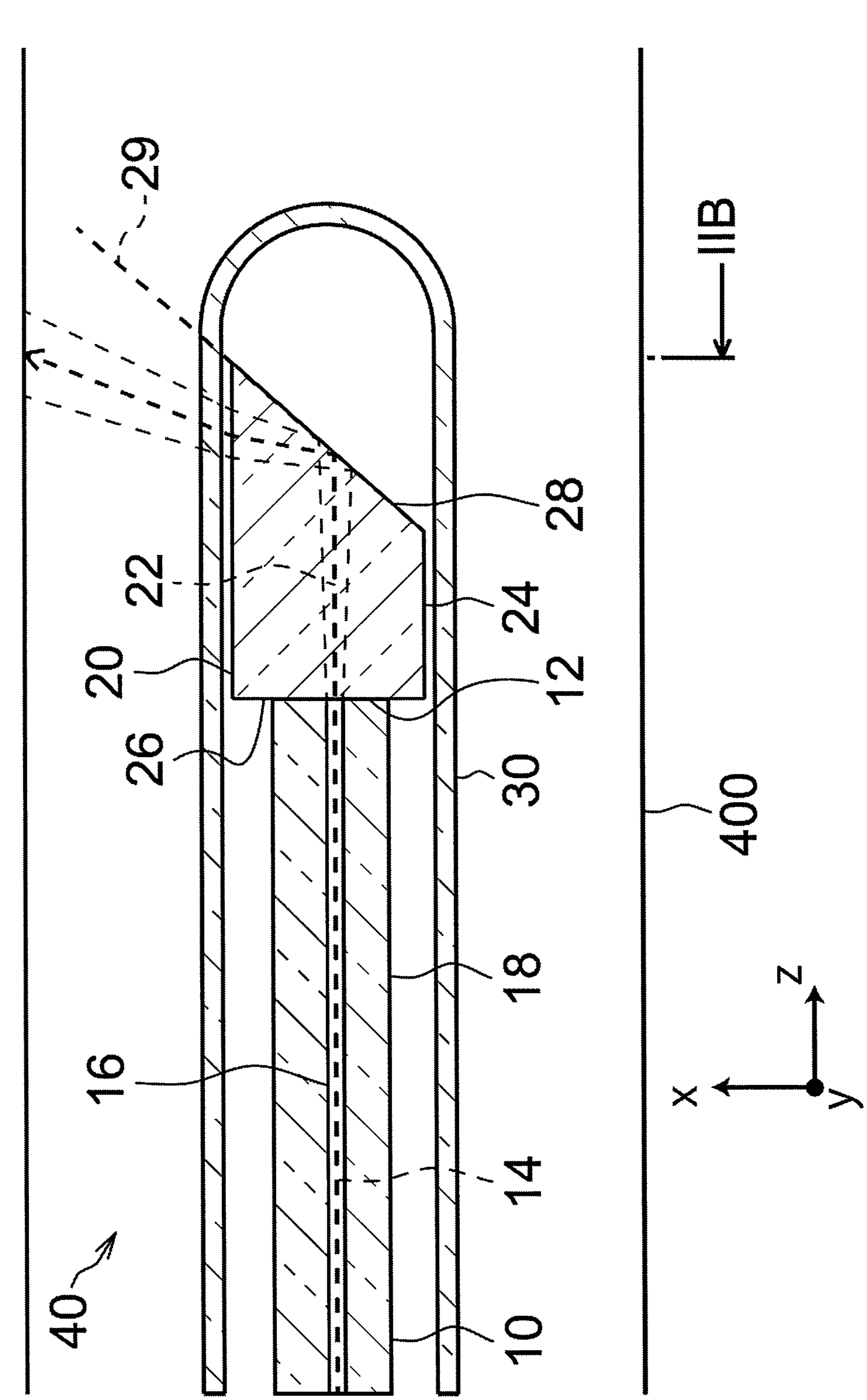
FIG. 2A is a cross-sectional view showing a schematic configuration of the optical probe shown in FIG. 1.
Figure 2B:
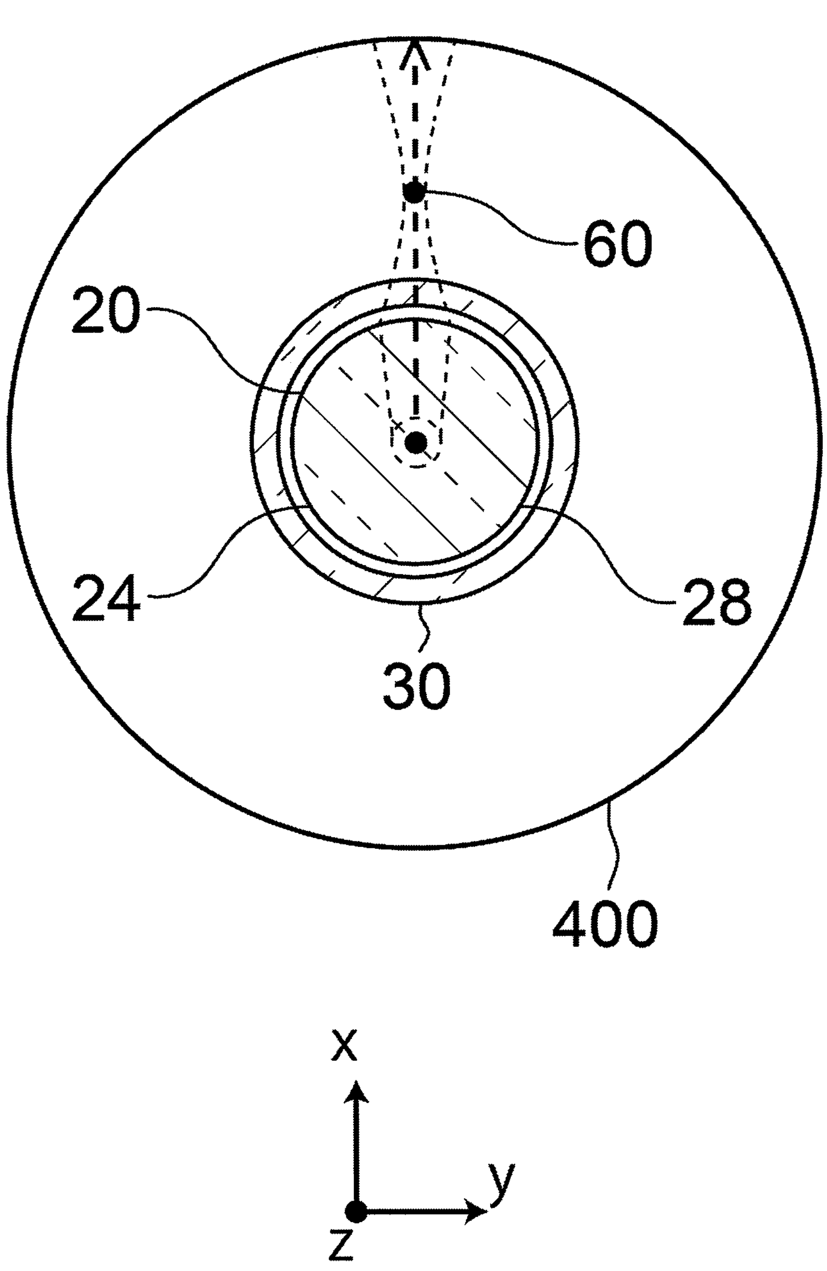
FIG. 2B is a cross-sectional view showing a schematic configuration of the optical probe shown in FIG. 1.

FIG. 2A shows a cross section along the axial direction of the optical probe 40 having a substantially cylindrical shape included in the optical tomographic imaging apparatus 100. FIG. 2B shows a cross section along the radial direction of the optical probe 40 having a substantially cylindrical shape. Hereinafter, an axial direction of the optical probe 40 is referred to as a "z direction", a front-back direction in FIG. 2A (or a left-right direction in FIG. 2B) orthogonal to the z direction is referred to as a "y direction", and a vertical direction in FIGS. 2A and 2B orthogonal to the z direction and the y direction is referred to as an "x direction".

The optical probe 40 includes an optical fiber 10 having a substantially cylindrical shape connected to the optical rotary joint 131 of the motor drive unit 130, a cylindrical lens 20 (lens member) connected to the tip surface 12 of the optical fiber 10 extending perpendicularly to the central axis 14 of the optical fiber 10 indicated by a broken line and optically coupled to the optical fiber 10, and a sheath 30 having a substantially cylindrical shape extending along the central axis 14 of the optical fiber 10 so as to cover the optical fiber 10 and the cylindrical lens 20.

The optical fiber 10 is formed of glass or resin having high transmittance, and includes a core 16 configured as a central portion extending along the central axis 14 of the optical fiber 10 and a clad 18 formed around the core 16. The refractive index of the core 16 is larger than the refractive index of the clad 18. Therefore, the optical fiber 10 is configured so that light passing through the inside thereof is concentrated on and transmitted through the core 16.

The cylindrical lens 20 is made of translucent glass, and has an outer circumferential cylindrical surface (cylindrical surface portion) 24 extending in the direction of the extension axis 22 parallel to the extension axis 22 obtained by forward-extending the central axis 14 of the optical fiber 10 indicated by a broken line, a rear end surface 26 extending perpendicular to the extension axis 22, and a tip surface 28 obliquely intersecting the extension axis 22. The outer circumferential cylindrical surface 24 of the cylindrical lens 20 has a diameter of, for example, about 200 to 400 μm. Therefore, the cylindrical lens 20 is very lightweight. In addition, the tip surface 28 of the cylindrical lens 20 is a flat surface being on the zx plane shown in FIG. 2A and extending along the inclined axis 29 obliquely intersecting the extension axis 22. As shown in FIG. 2B, the tip surface 28 has a substantially circular shape plane-symmetrical with respect to the zx plane (symmetry plane) including the extension axis 22 and the inclined axis 29. Furthermore, the tip surface 28 is configured so that light emitted from the tip surface 12 of the optical fiber 10 through the motor drive unit 130 is incident on the tip surface 28 along the extension axis 22 and light reflected by the tip surface 28 is emitted from the cylindrical lens 20 through the outer circumferential cylindrical surface 24.

In the embodiment, the tip surface 28 and the inclined axis 29 of the cylindrical lens 20 are inclined at an angle of 45° with respect to the extension axis 22. Accordingly, when the cylindrical lens 20 has a general refractive index of 1.43 to 2.14, the light incident on the tip surface 28 is totally reflected. In addition, the tip surface 28 and the inclined axis 29 of the cylindrical lens 20 may be inclined at an angle smaller than 45°, for example, 38° with respect to the extension axis 22. Accordingly, the light incident on the tip surface 28 is reliably totally reflected.

The optical fiber 10 and the cylindrical lens 20 are fused to each other at the tip surface 12 of the optical fiber 10 and the rear end surface 26 of the cylindrical lens 20. Since the optical fiber 10 and the cylindrical lens 20 are fused together, the mechanical strength of the optical probe 40 is improved. Therefore, there is no risk of losing an image due to peeling between the optical fiber 10 and the cylindrical lens 20 during capturing by the optical tomographic imaging apparatus 100.

In the embodiment, the refractive index of the core 16 of the optical fiber 10 and the refractive index of the cylindrical lens 20 are the same or substantially the same. Therefore, the light reflected at the boundary surface between the core 16 of the optical fiber 10 and the cylindrical lens 20 is reduced. Accordingly, an image of an object that does not actually exist (artifact) does not appear on the monitor of the signal processing unit 160.

In addition, the core 16 of the optical fiber 10 and the cylindrical lens 20 may be formed of pure quartz glass. Accordingly, light is not reflected between the optical fiber 10 and the cylindrical lens 20, and the above-described artifact does not reliably appear.

The sheath 30 is formed of a translucent resin, and is configured to transmit light emitted through the outer circumferential cylindrical surface 24 of the cylindrical lens 20. In addition, the inside of the sheath 30 is filled with a gas, for example, air. The inner diameter of the sheath 30 is larger than the outer diameters of the optical fiber 10 and the cylindrical lens 20 by, for example, about 50 μm. For example, when the outer diameter of the cylindrical lens 20 is about 200 to 400 μm, the inner diameter of the sheath 30 is about 250 to 450 μm. Therefore, the optical fiber 10 and the cylindrical lens 20 can freely move inside the sheath 30 along the central axis 14 of the optical fiber 10.

[Method for Optical Tomography]

Hereinafter, a method for optical tomography by the optical tomographic imaging apparatus 100 and the optical probe 40 will be described.

As shown in FIGS. 2A and 2B, the optical probe 40 covered with the sheath 30 is inserted into a predetermined position in a vessel, for example, the blood vessel 400.

As shown in FIG. 1, the optical tomographic imaging apparatus 100 emits light of a predetermined wavelength by turning on the low-coherence light source 110, and transmits the light to each of the motor drive unit 130 and the optical path adjustment unit 140 through the optical coupler 120.

The light sent to the motor drive unit 130 passes through the core 16 of the optical fiber 10 inside the optical probe 40 along the central axis 14 of the optical fiber 10 and travels toward the cylindrical lens 20 (see FIG. 2A). The light that has passed through the boundary between the tip surface 12 of the optical fiber 10 and the rear end surface 26 of the cylindrical lens 20 is incident on the tip surface 28 while diffusing, and is reflected there. As shown in FIG. 2A, the light reflected by the tip surface 28 diffuses while traveling in the radial direction (the radiation direction around the z axis) toward the outer circumferential cylindrical surface 24. Thereafter, the light reaches an outer circumferential cylindrical surface 24 having a circular cross-section, as shown in FIG. 2B. The outer circumferential cylindrical surface 24 functions as a convex lens surface. Therefore, the light reaching the outer circumferential cylindrical surface 24 is refracted on the outer circumferential cylindrical surface 24, passes through the sheath 30 while converging toward the focal point 60 being outside the sheath 30, and is applied to the blood vessel 400. The light reflected by the blood vessel 400 (reflected light) passes through the sheath 30 and is incident on the cylindrical lens 20 through the outer circumferential cylindrical surface 24. At this time, the reflected light incident on the cylindrical lens 20 is refracted and converged on the outer circumferential cylindrical surface 24 (convex lens surface), then reflected by the tip surface 28, passes through the coupling surface between the rear end surface 26 of the cylindrical lens 20 and the tip surface 12 of the optical fiber 10 along the extension axis 22, and is incident on the optical fiber 10. Thereafter, the reflected light is transmitted to the light receiving unit 150 through the optical fiber 10, the motor drive unit 130, and the optical coupler 120.

The optical tomographic imaging apparatus 100 performs tomographic capturing on the blood vessel 400 over the entire circumferential direction thereof. Therefore, the optical tomographic imaging apparatus 100 drives the optical probe rotary motor 134 of the optical probe drive unit 132 to rotate the optical fiber 10 at a high speed (preferably, about 180 rotations per 1 second) in the sheath 30. At the same time, the optical tomographic imaging apparatus 100 performs tomographic capturing on the blood vessel 400 continuously along the central axis 14 direction. Therefore, the optical tomographic imaging apparatus 100 drives the optical probe linear motor 138 of the optical probe linear drive unit 132 to retreat the optical fiber 10 in the sheath 30. Accordingly, the light emitted through the outer circumferential cylindrical surface 24 of the cylindrical lens 20 moves backward while scanning the entire circumferential direction of the blood vessel 400, and a blood vessel tomographic image continuous in the length direction of the blood vessel 400 is obtained. At this time, since the tip surface 28 of the cylindrical lens 20 to be rotated has a plane-symmetrical shape with respect to the zx plane (symmetry plane), the vibration of the cylindrical lens 20 that may occur when being rotated at a high speed can be suppressed as much as possible.

The light branched by the optical coupler 120 and sent to the optical path adjustment unit 140 is reflected by the reference mirror 144 into reference light. The reference light is superimposed on the reflected light sent from the optical probe 40 at the optical coupler 120. The coherent light in which the reference light and the reflected light are superimposed is transmitted to the light receiving unit 150.

The optical tomographic imaging apparatus 100 drives the mirror linear drive unit 146 according to the movement of the optical fiber 10 to move the reference mirror 144, and preferably keeps the optical path length from the optical coupler 120 to the reference mirror 144 equal to the optical path length from the optical coupler 120 to the tip surface 28. Accordingly, a tomographic image of the blood vessel 400 in which the positional relationship is easily intuitively understood can be obtained.

By receiving coherent light in the light receiving unit 150 and photoelectrically converting the coherent light, the optical tomographic imaging apparatus 100 transmits an electric signal including captured information to the signal processing unit 160, and reconstructs a tomographic image of the captured blood vessel to show the reconstructed tomographic image on the monitor.

As described above, according to the optical probe 40 of the embodiment, the light reflected by the inclined tip surface 28 of the cylindrical lens 20 is refracted by the cylindrical outer circumferential surface 24 and then collected toward the focal point 60 near the wall surface of the blood vessel 400. Therefore, the light reflected by the blood vessel 400 includes accurate blood vessel information. In addition, the light reflected by the blood vessel 400 is transmitted to the optical coupler 120 through the cylindrical lens 20 and superimposed on the reference light into coherent light in which only the reflected light at the capturing position is selectively amplified. Therefore, a clear tomographic image of the blood vessel 400 can be displayed on the monitor of the signal processing unit 160. In addition, since only the cylindrical lens 20 is present at the tip of the optical fiber 10 in the optical probe 40, the optical probe 40 has its tip allowed to be easily inserted into a small branch from a main branch at a bifurcation area of a vessel such as a blood vessel. In addition, since the number of connection surfaces of the optical element is kept to a minimum, the loss of light is suppressed low, and a bright image is obtained. Furthermore, since the mass of the lens member is sufficiently small, vibration during rotation can be suppressed as much as possible.

OTHER EMBODIMENTS

Figure 3A:
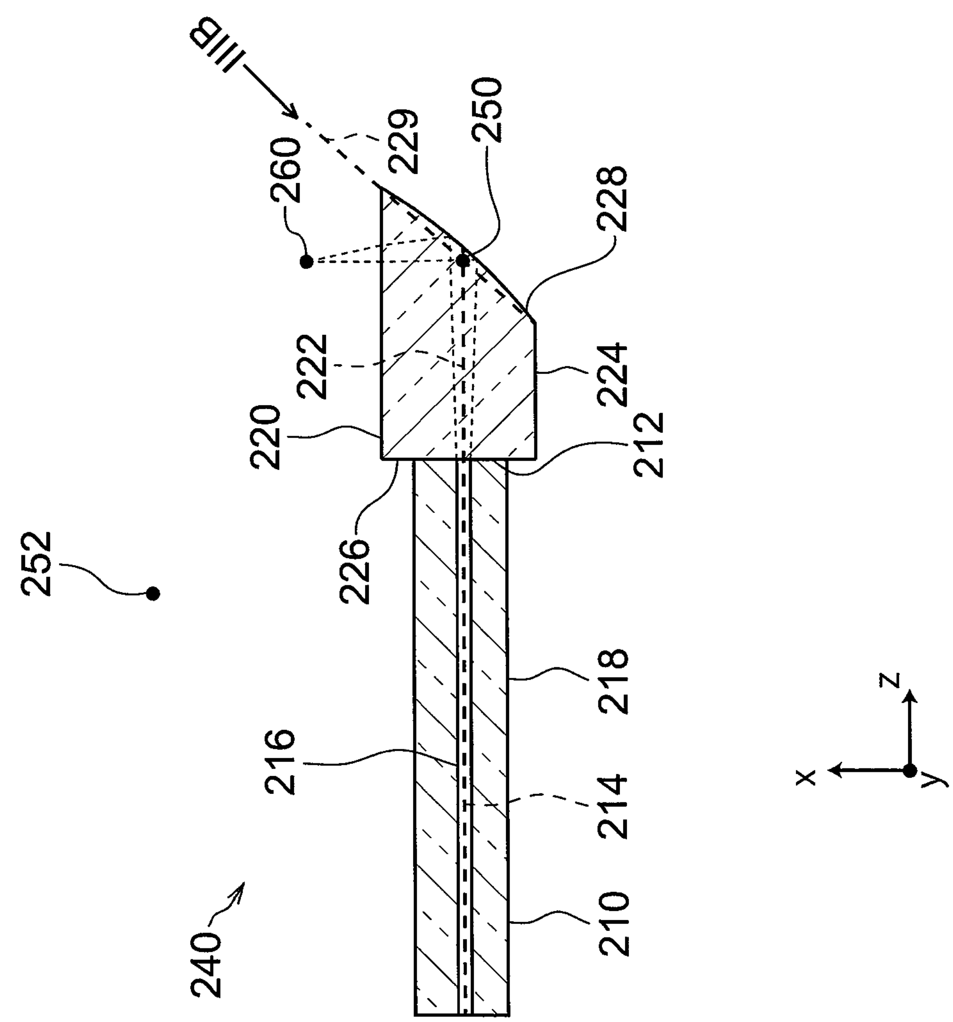
FIG. 3A is a cross-sectional view showing a schematic configuration of an optical probe according to another embodiment.

In the embodiment described above, the tip surface 28 of the cylindrical lens 20 is a flat surface extending along the inclined axis 29 that obliquely intersects the extension axis 22 of the optical fiber 10. However, as shown in FIG. 3A, the tip surface 228 of the cylindrical lens 220 may be a cylindrical surface about a virtual axis 252 that does not intersect the extension axis 222 and is parallel to the y direction. According to this embodiment, since not only the outer circumferential cylindrical surface 224 of the cylindrical lens 220 but also the tip surface 228 functions as a condenser lens, the light incident on the tip surface 228 is condensed in the radial direction by the tip surface 228. Therefore, at the time of capturing, the light emitted from the cylindrical lens 220 converges on the wall surface of the blood vessel or in the vicinity thereof. Therefore, the reflected light from the blood vessel includes more accurate blood vessel information, and as a result, accurate diagnosis is possible.

The length of the extension axis 222 from the rear end surface 226 to the tip surface 228 is preferably set to 0.4 to 0.6 mm. Accordingly, the light emitted from the cylindrical lens 220 reliably converges on the wall surface of the blood vessel or in the vicinity thereof.

In the above description, the optical fiber 10 and the cylindrical lens 20 are fused together at the tip surface 12 and the rear end surface 26 extending perpendicularly to the central axis 14 of the optical fiber 10 and the extension axis 22, but the tip of the optical fiber and the rear end surface of the cylindrical lens may be inclined surfaces positioned on the planes obliquely intersecting the central axis and the extension axis, respectively. Accordingly, the light reflected by the boundary surface between the core of the optical fiber and the cylindrical lens and incident on the optical coupler is reduced.

The tip surface 28 of the cylindrical lens 20 may be coated with a dielectric multilayer film, aluminum, silver, or gold. Accordingly, the light emitted from the tip surface 12 of the optical fiber 10 is easily reflected by the tip surface 28.

Although the cylindrical lens 20 of the optical probe 40 is formed of translucent glass, the cylindrical lens 20 may be formed of translucent plastic. Accordingly, the tip of the optical probe 40 is reduced in weight, and vibration during rotation can be further suppressed.

Figure 3B:
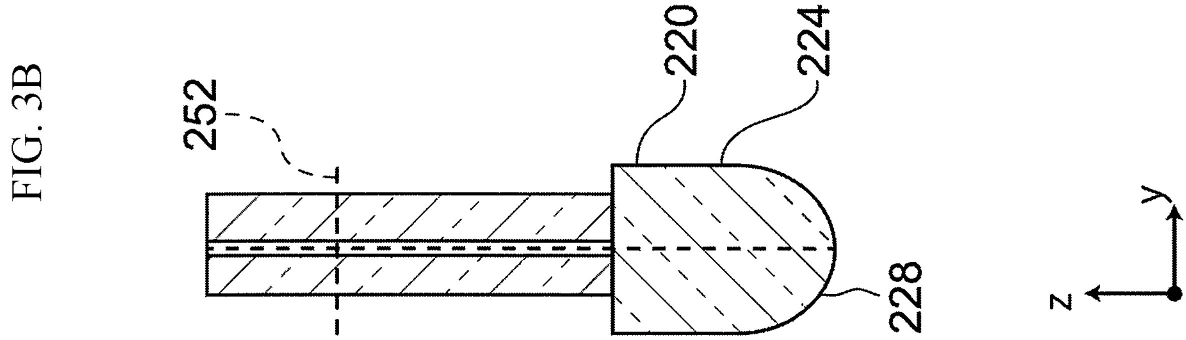
FIG. 3B is a cross-sectional view showing a schematic configuration of an optical probe according to another embodiment.

As shown in FIGS. 3A and 3B, the tip surface 28, 228 of the cylindrical lens 20, 220 may be a three-dimensional curved surface, for example, a toroidal curved surface, drawn by moving a cylindrical surface or a pseudo cylindrical surface (for example, an elliptical cylindrical surface) similar to the cylindrical surface being centered on a first virtual axis around a second virtual axis, the first virtual axis being on a plane including the central axis 14, 214 and the extension axis 22, 222 and being behind the tip surface 28, 228 (on the optical fiber side), the second virtual axis being orthogonal to the plane.

In the above-described embodiment, a cylindrical lens 20 having an outer circumferential cylindrical surface is used as the lens member provided at the tip of the optical fiber 10, but the entire periphery of the lens member does not need to be a cylindrical surface. For example, at least a portion where light reflected by the tip inclined surface of the lens member is emitted from the lens member may be a cylindrical surface, and the other portion may be a non-cylindrical surface. In this case, the outer circumferential cylindrical surface portion may be a cylindrical surface about the extension axis 22 extending the central axis 14 of the optical fiber 10 forward, a cylindrical surface about an axis parallel or substantially parallel to the extension axis 22, or a toroidal surface.

As described above, an optical probe used for a vascular optical tomographic imaging apparatus according to an embodiment of the present invention includes:

an optical fiber having a central axis; and a lens member having translucency fixed to a tip surface of the optical fiber, wherein the lens member has an outer circumferential surface surrounding an extension axis extending the central axis of the optical fiber, a rear end surface intersecting the extension axis, and a tip surface intersecting the extension axis, wherein a tip surface of the lens member is a surface extending obliquely with respect to the extension axis, wherein a rear end surface of the lens member is directly connected and optically coupled to a tip of the optical fiber, wherein the outer circumferential surface of the lens member has, at least in part, a cylindrical surface portion about the extension axis or a cylindrical surface portion about an axis parallel to the extension axis, and wherein light emitted from a tip of the optical fiber is configured to be incident on the tip surface along the extension axis, and light reflected by the tip surface is configured to be emitted from the lens member through the cylindrical surface portion.

Advantageous Effects of Invention

According to the optical probe according to the embodiment of the present invention, light emitted from the tip of the optical fiber is incident on the tip surface of the lens member, and light reflected by the tip surface is applied to a vessel such as a blood vessel through the cylindrical surface portion. The light reflected and scattered by the vessel is incident on the cylindrical surface portion of the lens member and converged toward the tip surface of the lens member. The light reflected by the tip surface of the lens member is converged toward the optical fiber. As described above, the cylindrical surface portion functions as a convex lens surface, and the light emitted from the cylindrical surface portion is converged toward the vessel. Therefore, the light reflected and scattered by the vessel includes accurate information on the vessel. In addition, since the optical probe does not include a component such as a rod type lens such as a GRIN lens, the optical probe can be easily inserted from a main branch into a small branch at a bifurcation area of a vessel such as a blood vessel. In addition, since the mass of the lens member is smaller than the mass of the ball lens, vibration during rotation can be suppressed as much as possible.

It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. An optical probe used for a vascular optical tomographic imaging apparatus, the optical probe comprising:

an optical fiber having a central axis; and a lens member made of a cylindrical glass lens having translucency fixed to a tip surface of the optical fiber, wherein the cylindrical glass lens has an outer circumferential surface surrounding an extension axis extending the central axis of the optical fiber, a rear end surface intersecting the extension axis, and a tip surface intersecting the extension axis, wherein the tip surface of the cylindrical glass lens is a substantially flat surface extending obliquely with respect to the extension axis, wherein the rear end surface of the cylindrical glass lens is directly connected to a tip of the optical fiber and optically coupled to the tip of the optical fiber, wherein the outer circumferential surface of the cylindrical glass lens has, at least in part, a cylindrical surface portion about the extension axis or a cylindrical surface portion about an axis parallel to the extension axis, and wherein the optical probe is disposed inside a sheath extending along the central axis of the optical fiber so as to cover the optical fiber and the lens member, wherein an inside of the sheath is filled with a gas, and wherein light emitted from a tip of the optical fiber is configured to be incident on the tip surface along the extension axis, and light reflected by the tip surface is configured to be emitted from the lens member through the cylindrical surface portion.

2. The optical probe according to claim 1, wherein the tip surface has a plane-symmetrical shape with respect to a symmetry plane including the extension axis and an inclined axis obliquely intersecting the extension axis.

3. The optical probe according to claim 2, wherein the inclined axis is inclined at an angle of 0° to 45° with respect to the extension axis.

4. The optical probe according to claim 1, wherein the tip surface of the optical fiber and the rear end surface of the cylindrical glass lens are respectively inclined surfaces positioned on surfaces obliquely intersecting the central axis and the extension axis.

5. The optical probe according to claim 1, wherein the tip surface is coated with a dielectric multilayer film, aluminum, silver, or gold.

6. The optical probe according to claim 1, wherein the lens member and a core of the optical fiber are formed of pure quartz glass.

7. The optical probe according to claim 1, wherein a diameter of the cylindrical surface of the cylindrical glass lens is between 200 μm and 400 μm.

8. The optical probe according to claim 7, wherein a length of the extension axis from the rear end surface to the tip surface of the cylindrical glass lens is between 0.4 mm and 0.6 mm.

9. An optical tomographic imaging apparatus comprising the optical probe according to claim 1.

10. The optical probe according to claim 1, wherein the lens member has a uniform refractive index.

11. The optical probe according to claim 1, wherein the lens member does not contain a GRIN lens.

12. The optical probe according to claim 2, wherein the inclined axis is inclined at an angle of 38° to 45° with respect to the extension axis.

* * * * *